United States Patent [19]

Alesandrini, Jr.

[11] 4,012,405

[45] Mar. 15, 1977

[54] PRODUCTION OF ETHYL CHLOROTHIOFORMATE

[75] Inventor: Carlo G. Alesandrini, Jr., Berkeley, Calif.

[73] Assignee: Stauffer Chemical Company, Westport, Conn.

[22] Filed: Nov. 28, 1975

[21] Appl. No.: 636,266

[52] U.S. Cl. .......................... 260/455 R; 260/608; 260/455 B

[51] Int. Cl.² ........................................ C07C 154/00

[58] Field of Search ................................ 260/455 R

[56] References Cited

UNITED STATES PATENTS

| | | | |
|---|---|---|---|
| 3,093,537 | 6/1963 | Tilles | 260/455 R |
| 3,165,544 | 1/1965 | Tilles | 260/455 R |
| 3,277,143 | 10/1966 | Tilles | 260/455 R |

*Primary Examiner*—Lewis Gotts
*Assistant Examiner*—D. R. Phillips
*Attorney, Agent, or Firm*—Joel G. Ackerman

[57] ABSTRACT

An improved process for producing ethyl chlorothioformate by the reaction of ethyl mercaptan with phosgene. The process is conducted in two stages, both occurring in a continuous liquid phase, in the presence of an activated carbon catalyst. Production of by-product diethyl disulfide is minimized and overall capacity can be increased.

14 Claims, 1 Drawing Figure

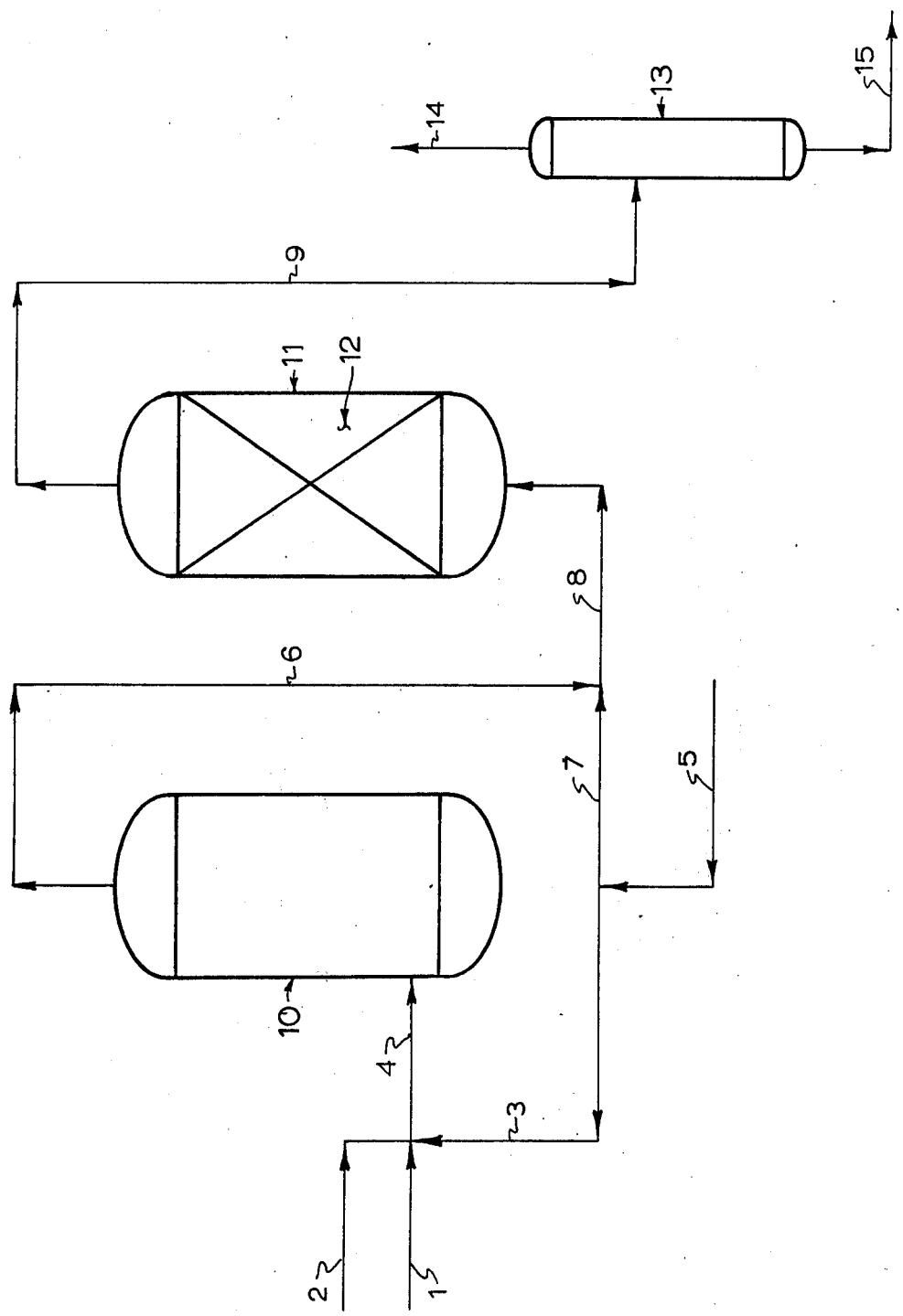

PRODUCTION OF ETHYL CHLOROTHIOFORMATE

BACKGROUND AND PRIOR ART

This invention relates to the production of ethyl chlorothioformate by the reaction of ethyl mercaptan with phosgene in the presence of an activated carbon catalyst,

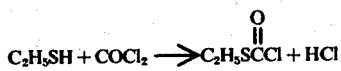

$$C_2H_5SH + COCl_2 \longrightarrow C_2H_5S\overset{\overset{O}{\|}}{C}Cl + HCl$$

Ethyl chlorothioformate is a useful intermediate for the production of herbicidally effective thiocarbamates. The reaction between ethyl mercaptan and phosgene to produce ethyl chlorothioformate is described in U.S. Pat. No. 3,165,544 of Harry Tilles, which discloses the conduct of this process in laboratory size equipment. It is pointed out that reaction temperatures should be maintained as low as possible, consonant with reasonable reaction rates since at high temperatures the alkyl disulfide by-product begins to form in significant amounts. Maximum temperature is suggested for this reaction using ethyl mercaptan at between about 75° and 140° C.

One process utilized for production of ethyl chlorothioformate by this reaction employs two catalytic beds of activated carbon arranged in series. The first bed is preferably contained in tubes of a multi-tube reactor; the second is in the form of a packed bed reactor containing a single catalyst bed. The first reactor is operated as a continuous liquid phase reactor; more specifically as an upflow tubular catalytic reactor, with starting materials introduced at the bottom and products removed from the upper portion. The partially reacted mixture is then introduced into the top of the second reactor, which functions as a trickle-flow (downflow) packed bed. That is, the second reactor is operated in the continuous gas phase since gaseous hydrogen chloride product is continuously passing upwardly through the bed. Reaction products are removed from the lower portion of the second reactor and passed to downstream apparatus for separating ethyl chlorothioformate. Operation of this process, however, has been found to produce ethyl chlorothioformate in a purity of only between about 91 and about 95%. The major impurity is diethyl disulfide, present in about 3–7%, with most of the remaining impurities being diethyl dithiocarbonate.

It is an object of the present invention to provide an improved process for the production of ethyl chlorothioformate by reaction of ethyl mercaptan and phosgene in the presence of an activated carbon catalyst.

A further objective of the present invention is to provide such a process with minimization of diethyl disulfide by-product.

A third objective of the present invention is to provide such a process with enhanced production capacity.

Yet another object of the present invention is to provide such a process having good temperature control in the reactors.

A still further objective of the present invention is to provide such a process having a good conversion of ethyl mercaptan to ethyl chlorothioformate.

SUMMARY OF THE INVENTION

The present invention comprises a process for production of ethyl chlorothioformate by the reaction of ethyl mercaptan with phosgene in the presence of an activated carbon catalyst comprising: (a) contacting ethyl mercaptan with phosgene in a first continuous liquid phase reaction zone in the presence of a catalyst comprising activated carbon; (b) removing a first reaction product from the first reaction zone; (c) contacting the first reaction product with a catalyst comprising activated carbon in a second continuous liquid phase reaction zone; and (d) removing a second reaction product comprising ethyl chlorothioformate from the second reaction zone.

DETAILED DESCRIPTION OF THE INVENTION

The invention is more particularly described with reference to the FIGURE, which shows a generalized flow sheet for the conduct of the process.

Referring to the FIGURE, ethyl mercaptan in line 1 is combined with phosgene in line 2 and the mixture introduced through line 4 into the lower portion of a first reactor 10. Reactor 10 is operated with reactants and products in a continuous liquid phase. Preferably, reactor 10 is a tubular packed bed reactor containing a plurality of tubes filled with activated carbon of an appropriate particle size such that each tube functions in the conventional manner as a miniature packed bed reactor. The reactants in stream 4 are introduced into the lower portion of the reactor, thereby into the lower portions of the individual tubes, and pass upwards through the tubes. The average outlet temperature is generally between about 0° and about 70° C, preferably between about 0° and about 50° C. Pressures range between about 0 and about 150 psig, preferably between about 0 and about 50 psig.

The partially reacted products from the first reactor 10 are removed from the upper part of this reactor as overhead in line 6 and passed through line 8 into a second reactor 11. Reactor 11 contains a packed bed 12 of activated carbon. The reaction is completed in reactor 11 in a continuous liquid phase. As shown in the FIGURE, this is accomplished by introducing reactants into the lower portion of reactor 11 so that this reactor operates in so-called "flooded upflow" condition. The reactor is generally operated at average outlet temperatures of between about 0° and about 70° C, preferably between about 10° and about 50° C, most preferably at a temperature within this range below 50° C. Pressures range between about 0 and about 150 psig, preferably between about 0 and about 50 psig. Residence time of the reactants in reactor 11 is generally between about 1 and about 180 minutes, preferably between about 5 and about 90 minutes.

The reaction products are removed from reactor 11 through overhead line 9, passed to separation drum 13 and product ethyl chlorothioformate is removed in line 15 for further purification. Gaseous by-products (primarily hydrogen chloride with some unreacted phosgene) are taken off at line 14 and passed to downstream purification units (not shown) for recovery of unreacted starting materials for recycle and removal and further processing of hydrogen chloride.

When, as in the prior process, the second reactor 11 is operated as a continuous gas phase reactor (e.g. as a trickle-flow packed bed reactor) the average outlet temperature can also be maintained at between about 0° C and about 70° C, as in the present process. However, operation according to the prior process results in an uneven temperature profile across the reactor due to poor heat transfer, providing localized high temperature zones, or "hot spots." It is known, from U.S. Pat. No. 3,165,544, that undesirably high temperatures contribute to the formation of by-product diethyl disulfide. The presence of hot spots in reactor 11, therefore, increases the possibility of formation of this by-product.

When the process is practiced using the present invention, however, the operation of the second reactor 11 as a continuous liquid phase packed bed reactor results in a marked decrease in diethyl disulfide formation since such operation provides better heat transfer and a more uniform temperature distribution throughout the catalyst bed.

Operation according to the present invention, with reactor 11 a continuous liquid phase reactor, results in an increase in the residence time in the second reaction at the same flow rate of the previous process, by a factor of at least about 10. Surprisingly, operation at such long residence times (for example, 45–90 minutes instead of 4–5 minutes) does not result in increased by-product formation so long as the temperature is maintained under good control. Alternatively, the flow rate of materials can be increased to permit operation at lower residence times in this reactor and increased capacity, as well as an increased conversion of ethyl mercaptan to the chlorothioformate. Preferably the flow rate can be increased up to 2–2½ times that used previously. At increased flow rates, residence time in the first reactor 10 is also decreased.

The desired temperature control in reactor 11 and in the overall process can be augmented by introduction of excess liquid phosgene into the system, either as part of the feed in line 2 or separately, into the reactor 10. Part or all of this excess will vaporize under the normal operating conditions of reactor 11, the vaporization absorbing heat generated during the reaction.

As an alternative method of temperature control, and also to assist in increasing the overall production of ethyl chlorothioformate, a relatively cold recycle stream 5, obtained from downstream processing units (not shown), and comprising primarily unreacted starting materials, can be introduced into the system. Preferably, the recycle stream in line 5 is introduced into reactor 11 via lines 7 and 8 and its presence contributes to the maintenance of a desirably low temperature in reactor 11, preferably one below about 50° C. Alternatively, recycle stream 5 can be introduced via lines 3 and 4 into the first reactor 10. Most preferably, temperature control is maintained by a combination of utilization of excess liquid phosgene and introduction of the recycle stream into reactor 11.

Operation according to the invention, as will be further seen from the example which follows, results in conversion of approximately 94% of starting ethyl mercaptan and production of a product of about 98% purity, containing generally less than 1% diethyl disulfide. Additonally, the use of a continuous liquid phase reactor, through the increase in residence time, provides greater capacity than a similar unit operating using a downflow or trickle flow packed reactor, in which the residence time is substantially shorter. As an alternative to the "flooded upflow" type of reactor shown in the FIGURE, reactor 11 can be operated as a continuous liquid phase reactor in any other manner as may be convenient, for example as a downflow flooded packed bed reactor.

The following examples illustrate the practice of the present invention.

EXAMPLE 1

A two-reactor system is utilized as shown in the FIGURE, having a capacity for production of about 57,000 pounds per day of ethyl chlorothioformate. The first reactor is a tubular upflow reactor, with the tubes packed with activated carbon catalyst. The second reactor is a packed bed reactor containing a bed of carbon catalyst and is operated as an upflow reactor.

Into the first reactor, corresponding to reactor 10 of the FIGURE, are fed 22.4 lb.-moles/hr. of phosgene and 20.4 lb.-moles/hr. of ethyl mercaptan. The reactor is operated at an inlet temperature of about 15°–40° C, an outlet temperature of about 50°–65° C, and an outlet pressure of about 30–36 psig. The partially reacted products from the first reactor are fed into the lower portion of the second reactor together with a recycle stream containing 10.7 lb.-moles/hr. phosgene and 4.7 lb.-moles/hr. ethyl chlorothioformate. The second reactor is operated at an inlet temperature of about 18°–26° C, an outlet temperature of about 33°–49° C, an outlet pressure of about 24–28 psig, and a residence time of about 75 minutes.

Conversion of ethyl mercaptan to the chlorothioformate was 94%. The product was produced in 98% purity, containing about 0.5–1% diethyl disulfide and about 1% diethyl dithiocarbonate.

EXAMPLE 2

The same system was utilized as in Example 1, but flow rates of materials were increased to provide a capacity of about 114,000 lbs./day of ethyl chlorothioformate. The flow rates of feed phosgene and ethyl mercaptan were respectively 44.8 and 40.8 lb.-moles/hr. The recycle flow rate was 21.4 and 9.4 lb. moles/hr. respectively of phosgene and ethyl chlorothioformate. Operating temperatures and pressures were substantially the same as in Example 1. The residence time of materials in the second reactor was reduced to about 35 minutes. The product ethyl chlorothioformate was again obtained in 98% purity, with 94% conversion of ethyl mercaptan. Diethyl disulfide content of the product was about 0.5–1%; diethyl dithiocarbonate content was about 0.5%.

What is claimed is:

1. A process for production of ethyl chlorothioformate comprising:
   a. contacting ethyl mercaptan with phosgene in a first continuous liquid phase reaction zone in the presence of a catalyst comprising activated carbon;
   b. removing a first reaction product from the first reaction zone;
   c. contacting the first reaction product with a catalyst comprising activated carbon in a second continuous liquid phase reaction zone; and
   d. removing a second reaction product comprising ethyl chlorothioformate from the second reaction zone.

2. A process according to claim 1 in which step (c) is operated at an average outlet temperature of between about 0° and about 70° C.

3. A process according to claim 1 in which step (c) is operated at an average outlet temperature of between about 10° and about 50° C.

4. A process according to claim 1 in which step (c) is operated at an average outlet temperature of between about 10° and below about 50° C.

5. A process according to claim 1 in which step (c) is operated at a residence time of between about 5 and about 90 minutes.

6. A process according to claim 5 in which step (c) is operated at a residence time of between about 45 and about 90 minutes.

7. A process according to claim 1 in which an excess of liquid phosgene is introduced into step (a).

8. A process according to claim 1 in which an excess of liquid phosgene is introduced into step (c).

9. A process according to claim 1 further comprising recovering unreacted starting materials from the product of step (d) and recycling said unreacted starting materials to step (c).

10. A process according to claim 1 further comprising recovering unreacted starting materials from the product of step (d) and recycling said unreacted starting materials to step (a).

11. A process according to claim 1 further comprising recovering ethyl chlorothioformate from the products of step (d).

12. A process according to claim 1 in which step (c) is conducted by introducing the first reaction product into the lower portion of a packed bed reactor containing a bed of activated carbon catalyst.

13. In a process for the production of ethyl chlorothioformate by the reaction of ethyl mercaptan with phosgene in the presence of a catalyst comprising activated carbon in a system comprising two reactors operating in a series, the improvement comprising operating the second reactor as a continuous liquid phase reactor.

14. A process according to claim 12 in which the second reactor is operated as a flooded upflow packed bed reactor.

* * * * *